United States Patent
Gao et al.

(10) Patent No.: US 11,179,579 B2
(45) Date of Patent: Nov. 23, 2021

(54) TOMOGRAPHIC IMAGING AND IMAGE-GUIDED RADIATION THERAPY APPARATUS

(71) Applicant: Tsinghua University, Beijing (CN)

(72) Inventors: Hewei Gao, Beijing (CN); Zhiqiang Chen, Beijing (CN); Li Zhang, Beijing (CN); Yuxiang Xing, Beijing (CN)

(73) Assignee: Tsinghua University, Beijing (CN)

( * ) Notice: Subject to any disclaimer, the term of this patent is extended or adjusted under 35 U.S.C. 154(b) by 0 days.

(21) Appl. No.: 16/966,547

(22) PCT Filed: Dec. 29, 2018

(86) PCT No.: PCT/CN2018/125565
§ 371 (c)(1),
(2) Date: Jul. 31, 2020

(87) PCT Pub. No.: WO2020/133400
PCT Pub. Date: Jul. 2, 2020

(65) Prior Publication Data
US 2021/0038920 A1    Feb. 11, 2021

(51) Int. Cl.
*A61B 6/00* (2006.01)
*A61N 5/10* (2006.01)
(Continued)

(52) U.S. Cl.
CPC ............ *A61N 5/1067* (2013.01); *A61B 6/032* (2013.01); *A61B 6/037* (2013.01); *A61B 6/4241* (2013.01);
(Continued)

(58) Field of Classification Search
CPC ............... A61N 5/1067; A61N 5/1049; A61N 2005/1052; A61N 2005/1087;
(Continued)

(56) References Cited

U.S. PATENT DOCUMENTS 6,449,331 B1   9/2002   Nutt et al.
7,001,045 B2   2/2006   Gregerson et al.
(Continued)

FOREIGN PATENT DOCUMENTS

CN   1762306 A   4/2006
CN   2910255 Y   6/2007
(Continued)

OTHER PUBLICATIONS

Chinese Office Action for Chinese Patent Application No. 201811653870.3 dated Oct. 27, 2020, 15 pages.
(Continued)

*Primary Examiner* — Kiho Kim
(74) *Attorney, Agent, or Firm* — Merchant & Gould P.C.

(57) ABSTRACT

An image-guided radiation therapy apparatus comprises: a high-energy ray source configured for radiation therapy of an object; and a KV ray source, a first and second PET detectors, and a CT detector for KV CT and PET imaging for guiding the radiation therapy. The KV ray source is placed on, or at an inner or outer side of the first PET detector; the second PET detector and the CT detector are configured to receive the KV ray to perform KV CT imaging; the PET detectors are further configured to receive gamma ray emitted by the object to perform PET imaging.

12 Claims, 5 Drawing Sheets

(51) Int. Cl.
*A61B 6/03* (2006.01)
*G01T 1/20* (2006.01)

(52) U.S. Cl.
CPC .......... *A61B 6/4266* (2013.01); *A61B 6/4291* (2013.01); *A61B 6/4435* (2013.01); *A61B 6/5235* (2013.01); *A61B 6/5282* (2013.01); *A61B 6/54* (2013.01); *A61N 5/1049* (2013.01); *G01T 1/2018* (2013.01); *A61N 2005/109* (2013.01); *A61N 2005/1052* (2013.01); *A61N 2005/1087* (2013.01)

(58) Field of Classification Search
CPC ...... A61N 2005/109; A61N 2005/1061; A61B 6/032; A61B 6/037; A61B 6/4241; A61B 6/4266; A61B 6/4291; A61B 6/4435; A61B 6/5235; A61B 6/5282; A61B 6/54; G01T 1/2018
See application file for complete search history.

(56) References Cited

U.S. PATENT DOCUMENTS

| | | | |
|---|---|---|---|
| 7,291,840 | B2 | 11/2007 | Fritzler et al. |
| 7,905,659 | B2 | 3/2011 | Gregerson et al. |
| 8,308,361 | B2 | 11/2012 | Gregerson et al. |
| 8,461,538 | B2 | 6/2013 | Mazin |
| 10,124,193 | B2 | 11/2018 | Ishikawa et al. |
| 10,231,678 | B2 | 3/2019 | Herrmann |
| 10,247,832 | B2 | 4/2019 | Serafino et al. |
| 10,327,716 | B2 | 6/2019 | Mazin |
| 10,537,299 | B2 | 1/2020 | Wang et al. |
| 2003/0235266 | A1 | 12/2003 | Gregerson et al. |
| 2006/0086905 | A1 | 4/2006 | Fritzler et al. |
| 2008/0212743 | A1 | 9/2008 | Gregerson et al. |
| 2011/0200175 | A1 | 8/2011 | Gregerson et al. |
| 2011/0301449 | A1* | 12/2011 | Maurer, Jr. ............ A61B 6/032 600/411 |
| 2011/0317812 | A1* | 12/2011 | Islam .................. A61B 6/5282 378/62 |
| 2013/0237818 | A1 | 9/2013 | Herrmann |
| 2015/0065870 | A1 | 3/2015 | Ishikawa et al. |
| 2017/0106208 | A1* | 4/2017 | Gauthier .............. A61N 5/1037 |
| 2018/0133518 | A1* | 5/2018 | Harper ................ A61N 5/1045 |
| 2018/0217273 | A1 | 8/2018 | Serafino et al. |
| 2018/0353147 | A1 | 12/2018 | Wang et al. |
| 2019/0070437 | A1* | 3/2019 | Olcott ................ A61N 5/1075 |
| 2019/0091487 | A1* | 3/2019 | Pal ...................... A61N 5/1031 |
| 2019/0143145 | A1* | 5/2019 | Laurence, Jr. ......... A61B 34/10 600/1 |
| 2019/0255362 | A1* | 8/2019 | Voronenko ........... A61N 5/1049 |

FOREIGN PATENT DOCUMENTS

| | | |
|---|---|---|
| CN | 101756711 A | 6/2010 |
| CN | 103143124 A | 6/2013 |
| CN | 104136078 A | 11/2014 |
| CN | 107923982 A | 4/2018 |
| EP | 2 520 335 A1 | 11/2012 |
| JP | 2006-068102 A | 3/2006 |
| WO | 03/103496 A1 | 12/2003 |
| WO | 2016/197127 A1 | 12/2016 |

OTHER PUBLICATIONS

Response to Chinese Office Action for Chinese Patent Application No. 201811653870.3 filed Nov. 11, 2020, 31 pages.
International Search Report and Written Opinion of the International Searching Authority for International Patent Application No. PCT/CN2018/125565 dated May 24, 2019, 8 pages.
Berard, P. et al., "CT Acquisition Using PET Detectors and Electronics", IEEE Transactions on Nuclear Science, 52(3):634-637 (2005).
Bergeron, M. et al., "LabPET II, and APD-based Detector Module with PET and Counting CT Imaging Capabilities", IEEE Transactions on Nuclear Science, 62(3): 756-765 (2015).
Fan, Q. et al., "Emission guided radiation therapy for lung and prostate cancers: A feasibility study on a digital patient", Med. Phys., 39(11): 7140-7152 (2012).
Fan, Q. et al., "Toward a planning scheme for emission guided radiation therapy (EGRT): FDG based tumor tracking in a metastatic breast cancer patient", Med. Phys. 40(8): 081708-1-081708-12 (2013).
Jaffray, D. et al., "Flat-Panel Cone-Beam Computed Tomography for Image-Guided Radiation Therapy", Int. J. Radiation oncology Biol. Phys., 53(5): 1337-1349 (2002).
Kapoor, V. et al., "An Introduction to PET-CT Imaging", Radio Graphics, 24(2): 523-543 (2004).
Mackie, T.R., "History of tomotherapy", Phys. Med. Biol., 51: R427-R453 (2006).
Xing, L. et al., "Overview of Image-Guided Radiation Therapy", Medical Dosimetry, 31 (2): 91-112 (2006).

* cited by examiner

TOMOGRAPHIC IMAGING AND IMAGE-GUIDED RADIATION THERAPY APPARATUS

This application is a National Stage Application of PCT/CN2018/125565, filed 29 Dec. 2018, and which application is incorporated herein by reference. A claim of priority is made to the above disclosed application.

TECHNICAL FIELD

The present disclosure relates to the field of medical imaging and radiation therapy guidance, particularly to a tomographic imaging and image-guided radiation therapy apparatus.

BACKGROUND

Radiation therapy is one of main ways to treat malignant tumors at present. In the radiation therapy, image guidance is one of the key means to ensure high-precision therapy. The radiation therapy guidance is essentially to obtain accurate position information of a body of a patient by means of medical imaging before or in therapy, to reduce therapy errors caused by placement of the body of the patient, and movements of organs of the patient such as heartbeat and breathing, thereby improving or ensuring the accuracy of the radiation therapy. At present, the most common radiation therapy is to use megavolt (MV) high-energy X-rays, and the most common radiation therapy guidance is computerized tomographic (CT) based on kilovolt (KV) X-rays. In recent years, radiation therapy based on magnetic resonance imaging (MRI) guidance has also been successfully developed and applied in clinics. Meanwhile, scientists and engineers are also actively developing new radiation therapy mode based on positron emission tomography (PET) guidance.

The PET is a kind of functional imaging, which can obtain biological information of human body. In the PET imaging, gamma photons produced by positron annihilation have a potential to directly reflect real-time location information of the tumor in the body of the patient. The real-time location information of the tumor is of great significance for high-precision therapy of the tumor. The movements of the patient's organs in therapy have been a major challenge for the radiation therapy. Therefore, the PET-guided radiation therapy apparatus has strong clinical application potential, and is also one of hotspots and difficulties that are currently being studied in academia and industry. In the PET-guided radiation therapy apparatus, due to the physical mechanism of the PET imaging, the PET cannot alone give the accurate information of the contour of the body of the patient lying on a therapy bed. At the same time, the PET usually also needs to use CT images to achieve attenuation correction and the like. Therefore, similar to the PET/CT in medical diagnosis, the PET-guided radiation therapy apparatus usually also needs the CT to "assist" the PET imaging.

In summary, the CT imaging plays an important role in the radiation therapy system. At present, the common CT subsystems mainly have two modes: a kilovolt CT (KVCT) and a megavolt CT. Among them, a high-energy X-ray (megavolt) source in the therapy, i.e. a medical linear accelerator is usually directly used in the megavolt CT. The scanning plane of the megavolt CT is naturally in the same plane as the therapy, which brings great convenience to the image registration, and at the same time is beneficial to optimize the therapy plan. However, the quality of imaging of the megavolt CT is not high. A reconstructed image has a low contrast and the patient receives a large dose of radiation. Unlike the megavolt CT, a separate, medical diagnostic (kilovolt) X-ray source is generally used in the kilovolt CT. The kilovolt CT can in turn be subdivided into two categories, i.e., a cone beam CT based on a flat detector and a diagnostic CT based on a plurality of rows of spiral CT detectors. The kilovolt CT has advantages such as a low dose of radiation and a high contrast.

In a currently existing PET-guided radiation therapy system design, since the PET imaging and therapy must be performed in the same plane, with the limitations imposed by a spatial location, an independent kilovolt CT subsystems cannot share a single scanning plane with the therapy and the PET imaging, which imposes many restrictions on radiation therapy and guidance. The restrictions are mainly reflected in that when the patient and the therapy bed are switched between the CT imaging and the PET imaging or therapy, the back and forth movement of the patient and the therapy bed easily causes changes in the positions of the human organs, so that the imaging cannot be carried out simultaneously or in real time in the therapy, which limits the process and implementation of the therapy.

With the development of the radiation therapy to a spiral therapy mode based on a rotating gantry, and the urgent need for an "adaptive" therapy plan, coplanar image guidance and therapy will surely be the future trend of the radiation therapy and also the inevitable result of precise radiation therapy.

The image-guided radiation therapy apparatus based on the rotating gantry has relatively large and complicated equipment. The image-guided radiation therapy apparatus is generally composed of a high-energy ray source that can be used for therapy and its auxiliary collimating subsystem, an imaging subsystem, a rotating gantry, a therapy bed, a high-energy detector, a computer control and data processing subsystem, and the like. The main function of the imaging subsystem is image guidance, which can generally be used to locate the body of the patient before the therapy, and obtain information such as the movement of the body and the displacements of the organs in the therapy, and then feed them back to the therapy subsystem to guide the therapy to become more efficient and accurate.

At present, there are mainly two limiting factors for the quality of the CT imaging of the existing CT imaging and image-guided radiation therapy apparatus based on a PET detector: 1) a single pixel unit of the PET detector is generally larger than a single pixel unit of a CT detector, and 2) there is generally no de-scattering collimation for the PET detector. These limiting factors will result in a lower spatial resolution, a larger scattering artifact, and a lower detection sensitivity of the CT imaging.

SUMMARY

Embodiments of the present disclosure provide a tomographic imaging and image-guided radiation therapy apparatus comprising:

at least one high-energy ray source;

at least one KV ray source for providing KV ray for medical diagnosis;

a first PET detector located on a side close to the at least one KV ray source;

a second detector located on a side away from the at least one KV ray source and at the side opposite to the KV ray source; and a CT detector located at the side opposite to the KV ray source and configured to receive the KV ray for CT imaging;

wherein the at least one KV ray source is placed on or at an inner side of or at outer side of the first PET detector;

the second PET detector and the CT detector are configured to receive the KV ray to perform a KV CT imaging;

the first PET detector and the second PET detector are further configured to receive a gamma ray emitted by an object to perform a PET imaging;

the high-energy ray source is configured to generate a high-energy ray for radiation therapy of the object;

the KV CT imaging of the CT detector and the second PET detector and/or the PET imaging of the first PET detector and the second PET detector are configured to assist and/or guide the radiation therapy of the object.

In some embodiments of the present disclosure, there is an intersection point between a straight line where a focal point of the KV ray source and a center of the object are located and the CT detector, and a distance between the intersection point and a center of the CT detector is not greater than a half of a length of the CT detector.

In some embodiments of the present disclosure, the focal point of the KV ray source, the center of the object, and a position offset from the center of the CT detector by (n+1/4)×a lie on a same straight line, where a is a detector pixel of the CT detector, n is an integer, and 0≤n≤8.

In some embodiments of the present disclosure, the CT detector is an energy integrating detector or a photon counting detector; and/or the KV ray source comprises one of an X-ray tube, a carbon nanotube, or an isotope source; the KV ray is an X-ray or a gamma ray; and/or the high-energy ray source comprises an accelerator or an isotope source for radiation therapy, the high-energy ray comprises one of a MV photon ray or a MV particle ray, and the MV photon ray comprises one of a MV X-ray or a gamma ray; and the MV particle ray comprises one of a proton, a neutron or a carbon ion.

In some embodiments of the present disclosure, the first PET detector and the second PET detector are composed of a plurality of PET detection modules and/or a plurality of detection units, there is gap between adjacent ones of the PET detection modules and/or the detection units, and the first PET detector and the second PET detector have an arc shape, a straight line shape, or a polygonal shape.

In some embodiments of the present disclosure, the CT detector is equipped with at least one de-scattering processing unit with a function of removing scattered photons, a spatial structure of the de-scattering processing unit is a one-dimensional fence or a two-dimensional grid, and a material of the fence and/or the grid is a metal with a high atomic number.

In some embodiments of the present disclosure, the CT detector has the same detector pixel and Scintillator thickness and is of the same type as the PET detector.

In some embodiments of the present disclosure, the CT detector is a flat detector with a high spatial resolution, the high spatial resolution means that a detector pixel of the flat detector is not greater than 1 mm, and the CT detector is further configured to receive the KV ray to perform a single-frame or multi-frame transmissive imaging.

In some embodiments of the present disclosure, the second PET detector and the CT detector are configured to receive the KV ray to perform the KV CT imaging in such a way that the CT detector receives the KV ray, a scattering correction is performed on the KV ray received by the second PET detector, and data and/or image are combined and processed to determine a full-field KV CT imaging; or the second PET detector receives the KV ray, a data truncation correction and a scattering correction optimization is performed on the KV ray received by the CT detector to determine a KV CT imaging of a partial field of view.

In some embodiments of the present disclosure, the apparatus further comprises at least one high-energy detector placed opposite to the high-energy ray source and configured to receive a high-energy ray;

the high-energy detector, the high-energy ray source, the first PET detector, the second PET detector and the CT detector, and the KV ray source are located in a same plane; and the first PET detector and the second PET detector are located on two sides of the high-energy ray source and the high-energy detector, respectively.

In some embodiments of the present disclosure, the apparatus further comprises: a rotating gantry configured to carry the first PET detector, the second PET detector, the CT detector, the high-energy ray source and the KV ray source, and rotate the first PET detector, the second PET detector, the CT detector, the high-energy ray source and the KV ray source around the object; and a mechanical/electrical control and data transmission/processing unit configured to control the rotating gantry, the first PET detector, the second PET detector, the CT detector, the high energy ray source and the KV ray source, and transmit and process data detected by the first PET detector, the second PET detector, the CT detector.

Compared with the prior art, the tomographic imaging and image-guided radiation therapy apparatus according to the present disclosure has at least the following advantages.

1. The CT detector is disposed between the first and second PET detectors, which helps to improve the detection sensitivity of the tomographic imaging and image-guided radiation therapy apparatus, and at the same time helps to improve the spatial resolution of the CT imaging and reduce scattering artifacts, without significantly reducing the performance of the PET imaging of the system.

2. Since the PET detector generally does not have a ray-removing collimator, and directly receive the KV ray, the influence of scattered photons on the PET detector may be relatively serious, which is easy to bring artifacts to a KV CT image. Therefore, the CT detector is provided with a de-scattering processing unit, which can effectively prevent indirect X-rays from entering the CT detector, and can further improve the accuracy of the KV CT imaging, thereby reducing the scattering artifacts.

3. The second PET detector and the CT detector receive the KV ray to perform the KV CT imaging. There are two ways of cooperation between the CT detector and the PET detector: the CT detector receives the KV ray, a scattering correction is performed on the KV ray received by the second PET detector, and data and/or image are combined and processed to determine a KV CT imaging of a full field of view; or the second PET detector receives the KV ray, a data truncation correction and a scattering correction optimization is performed on the KV ray received by the CT detector to determine a KV CT imaging of a partial field of view, which can be selected by a user according to requirements.

DETAILED DESCRIPTION

In the prior art, the tomographic imaging and image-guided radiation therapy apparatus based on the PET detector has defects of a low spatial resolution of the CT imaging, a large scattering artifact, and a low detection sensitivity. In view of this, In order that the object, technical solutions and advantages of the present disclosure are more apparent and more readily appreciated, the present disclosure will be further described in detail in conjunction with embodiments with reference to the accompanying drawings as below.

Embodiments of the present disclosure provide a tomographic imaging and image-guided radiation therapy apparatus comprising: at least one high-energy ray source configured for emitting high-energy ray for radiation therapy; at least one KV ray source 20 for providing KV ray for medical diagnosis; a first PET detector 31 and a second PET detector 32 placed opposite to each other, the first PET detector 31 being located on a side close to the KV ray source, the second PET detector 32 being located on a side far from the KV ray source, and a CT detector 21 located away from the KV ray source and at the side opposite to the KV ray source. In an embodiment, the second PET detector 32 may include at least two sections of PET detectors and the CT detector 21 is located between the at least two sections of PET detectors. The at least one medical diagnostic KV ray source is placed on or at an inner side of or at outer side of the first detector on the first detector and configured to generate a KV ray; the second PET detector 32 is configured to receive the KV ray to perform a KV CT imaging; the first PET detector 31 and the second PET detector 32 are further configured to receive a gamma ray emitted by an object to perform a PET imaging. Here, it is noted that an object may be provided a source that is capable of emitting GAMMA ray (for example, a human may take a source) under a ray inspection. The high-energy ray source is configured to generate a high-energy ray for radiation therapy of the object; the KV CT imaging and/or the PET imaging are configured to assist and/or guide the radiation therapy of the object.

Figure 1:
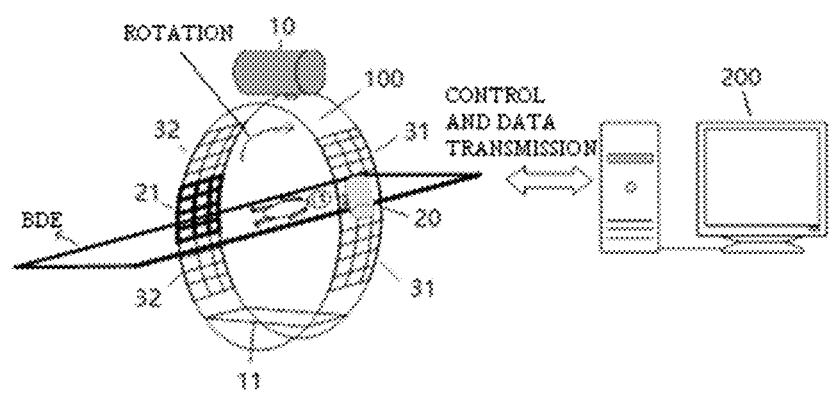
FIG. 1 is a schematic perspective view of a tomographic imaging and image-guided radiation therapy apparatus according to a first embodiment of the present disclosure.
Figure 2:
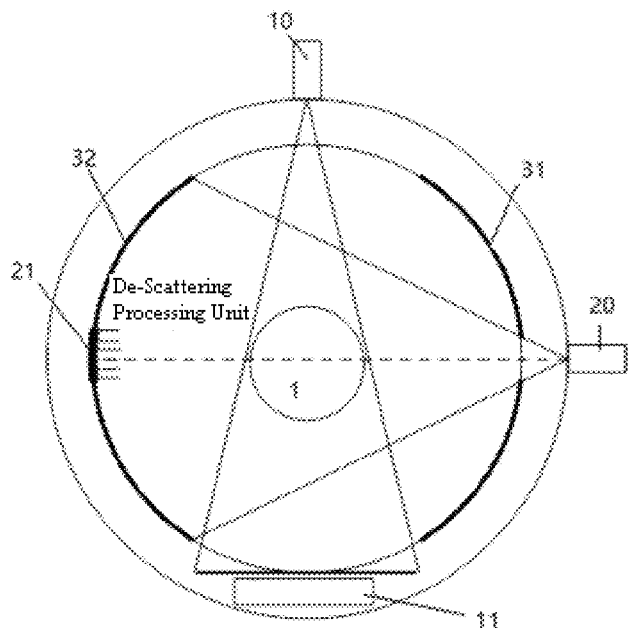
FIG. 2 is a schematic view showing a structure of a first implementation of FIG. 1.
Figure 3:
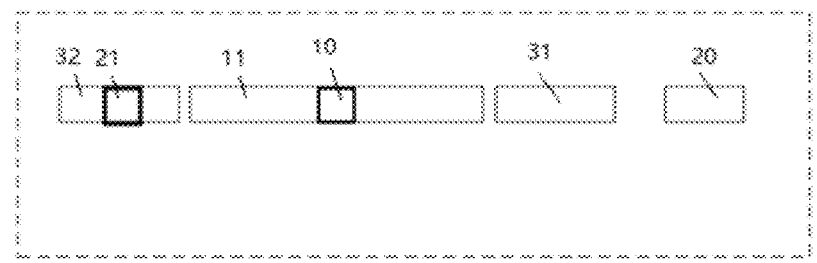
FIG. 3 is a top view of FIG. 2.
Figure 4:
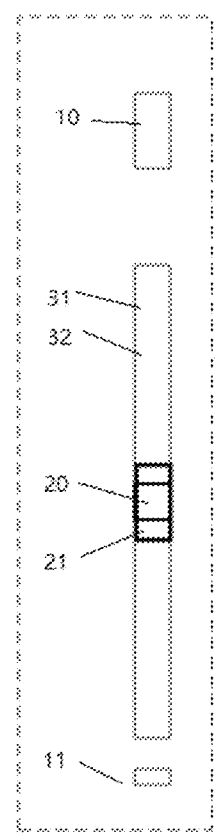
FIG. 4 is a side view of FIG. 2.

FIG. 1 is a schematic perspective view of a tomographic imaging and image-guided radiation therapy apparatus according to a first embodiment of the present disclosure, FIG. 2 is a schematic view showing a structure of a first implementation of FIG. 1, FIG. 3 is a top view of FIG. 2, and FIG. 4 is a side view of FIG. 2. As shown in FIGS. 1 to 4, A description will be made as below by taking a single KV ray source placed on the first detector as an example.

In the above embodiment, the CT detector 21 is disposed between the second PET detectors 32, which helps to improve the detection sensitivity of the tomographic imaging and image-guided radiation therapy apparatus, and at the same time helps to improve the spatial resolution of the CT imaging and reduce scattering artifacts, without significantly reducing the performance of the PET imaging of the system.

The high-energy ray source in the embodiments of the present disclosure may be an accelerator or an isotope source (or other devices) for radiation therapy, and is configured to generate one of a million voltage order MV photon ray or a MV particle ray, and the MV photon ray comprises one of a MV X photon or a gamma ray; and the MV particle ray comprises one of a proton, a neutron or a carbon ion.

The KV ray source comprises one of an X-ray tube, a carbon nanotube, or an isotope source; and accordingly the KV ray is mainly an X-ray, but may also be a gamma ray generated by the isotope and having an energy in a medical diagnostic range. The KV ray source refers to a ray source in which a voltage between a cathode and an anode is in a kilovolt level/order, including a ray source in the kilovolt level, which can be set and adjusted according to needs. For example, it may be a commonly used ray source with thousands of voltages to more than one hundred voltages.

In some embodiments of the present disclosure, the CT detector may be an energy integrating detector or a photon counting detector. The CT detector may be a flat detector with a high spatial resolution, and the high spatial resolution means that a detector pixel of the flat detector is not greater than 1 mm, so that the CT detector is capable of being configured to receive the KV ray to perform a single-frame or multi-frame transmissive imaging.

The first PET detector 31 and the second PET detectors 32 are both composed of a plurality of PET detection modules and/or a plurality of PET detection units, and there is gap between adjacent ones of the PET detection modules and/or the detection units (regardless of whether or not the gaps are uniform). In the embodiment, the first and the second PET detectors 31, 32 have an arc shape, a straight line shape, or a polygonal shape. Preferably, the CT detector 21 has the same detector pixel and Scintillator thickness and is of the same type as the first and the second PET detectors. Thereby, the first and the second PET detectors 31, 32 can be compatible with the CT detector 21 to avoid large errors. If the detector pixels, and the Scintillator thickness and type of the CT 21 detector and the first and the second PET detectors 31, 32 are inconsistent, the cooperation between the first and the second PET detectors 31, 32 and the CT detector 21 can also be achieved, but the compatibility effect is sacrificed and the error is large.

In FIG. 2, the positional relationship between the CT detector 21 and the second PET detectors 32 of the second detector is as follows: there is an intersection point between a straight line where a focal point of the KV ray source 20 and a center of the object 1 are located and the CT detector 21, and a distance between the intersection point and a center of the CT detector 21 is not greater than a half of a length of the CT detector 21.

In an embodiment, the focal point of the KV ray source 20, the center of the object 1, and a position offset from the center of the CT detector 21 by $(n+1/4) \times a$ lie on a same straight line, where a is a detector pixel of the CT detector 21, n is an integer, and $0 \leq n \leq 8$. In this way, the CT detector 21 can more effectively perform an imaging, the detection sensitivity of the tomographic imaging and image-guided radiation therapy apparatus can be improved, and at the same time it helps to improve the spatial resolution of the CT imaging and reduce the scattering artifacts.

In addition, since the PET detector does not have the ray collimating function, and directly receive the KV ray, the influence of scattered photons on the PET detector may be relatively serious, which is easy to bring artifacts to a KV CT image. Therefore, the CT detector 21 may further be provided with at least one de-scattering processing unit with a function of removing scattered photons, thereby improving the imaging performance of the KV CT. A spatial structure of the de-scattering processing unit may be a one-dimensional fence or a two-dimensional grid (preferably, a structure with a large "depth-to-width ratio", such as a depth-to-width ratio of about 15), and a material of the fence and/or the grid may be an element with a high atomic number, such as tungsten and molybdenum. In addition, the de-scattering processing unit may also be a software algorithm unit. A user can choose one or both of the two ways according to actual situations.

The second PET detector 32 and the CT detector 21 receive the KV ray to perform the KV CT imaging. There may be two ways of cooperation between the CT detector 21 and the second PET detector 32: the CT detector 21 receives the KV ray, a scattering correction is performed on the KV ray received by the second PET detector 32, and data and/or image are combined and processed to determine a KV CT imaging of a full field of view; or the second PET detector 32 receives the KV ray, a data truncation correction and a scattering correction optimization is performed on the KV ray received by the CT detector 21 to determine a KV CT imaging of a partial field of view.

Thereby, when the KV CT imaging is performed, the KV ray source 20 and the second PET detector 32, the CT detector 21 are rotated relative to the object around the object to obtain KV CT projection data at different rotation angles. The user can choose the cooperation way according to the requirements, and then obtain a KV CT image in a different form through an external computer operation.

In FIG. 1, a helical scanning (therapy) mode based on the rotating gantry is generally adopted in the tomographic imaging and image-guided radiation therapy apparatus. Because the requirements of the apparatus for the spatial resolution/the density resolution and the like of the KV CT imaging will not be too high (relative to a medical diagnostic CT), its universality is extremely strong.

In the first embodiment, the KV ray source 20 is placed at the outer side of the first PET detector 31 (the side away from the object). In order to allow the KV ray to reach the second PET detector 32 and the CT detector 21, it is necessary to provide a certain gap or opening in the first first detector 31 so that the KV ray irradiates the second PET detector 32 and the CT detector 21 through the opening or the gap.

In the present embodiment, for the KV ray source 20, all conventional ways for reducing the CT dose can be directly used, such as bowtie filtering and front collimation. The KV ray source 20 may be a conventional ray source such as an X-ray tube, a new ray source such as a carbon nanotube, or an isotope source, or the like, and is not limited in the present disclosure.

Since the first PET detector 31 and/or the second PET detector 32 can also receive 511 KeV gamma rays emitted by the object (including a tracer agent), the PET imaging can be performed, and at the same time, in combination with the CT imaging, a co-detector function can be achieved, which can have characteristics of a high contrast and a strong practicability in the case where the radiation dose is small.

Similar to the radiation therapy apparatus in the prior art, the radiation therapy apparatus involved in the present disclosure generally further includes at least one high-energy detector 11. Referring to FIG. 1, the high-energy detector 11 is located in a middle position between the first PET detector 31 and the second PET detector 32, is placed opposite to the high-energy ray source 10 and is configured to receive a high-energy ray;

In addition, as shown in FIG. 1, the tomographic imaging and image-guided radiation therapy apparatus according to the present disclosure is based on the spiral scanning (therapy) mode of the rotating gantry, and further includes:

a rotating gantry configured to carry the first PET detector 31, the second PET detector 32, the high-energy ray source 10 and the KV ray source 20, and rotate the first PET detector, the second PET detector, the high-energy ray source 10 and the KV ray source 20 around the object; and a mechanical/electrical control and data transmission/processing unit configured to control the rotating gantry, the first PET detector, the second PET detector 32, the CT detector 21, the high energy ray source 10 and the KV ray source 20 (for example, rotations of the rotating gantry, the first PET detector 31, the second PET detector 32, the CT detector 21, the high energy ray source 10 and the KV ray source 20, and emissions of rays of the high energy ray source 10 and the KV ray source 20), and transmit and process data detected by the first PET detector 31 and the second PET detector 32, the CT detector 21.

Referring to FIGS. 3 and 4 again, in the present disclosure, the first PET detector 31 and the second PET detector 32, the CT detector 21, the KV ray source 20, the high-energy detector 11 and the high-energy ray source 10 can lie in the same plane, and the first PET detector 31 and the second PET detector 32, the KV ray source 20 are located on two sides of the high-energy ray source 10 and the high-energy detector 11, respectively, which brings great convenience to the image registration and at the same time facilitates optimizing the therapy plan.

It should also be noted that the tomographic imaging and image-guided radiation therapy apparatus according to the present disclosure can performing an imaging before or after therapy, and the imaging can be performed in a plurality of modes:

before and/or after therapy, the first PET detector 31 and/or the second PET detector 32, the KV ray source 20 are set to an integration mode, and the KV rays are emitted to realize an independent cone beam, fan beam or spiral CT scanning; and/or before and/or after therapy, the first PET detector 31 and/or the second PET detector 32, the KV ray source 20 are set to a counting mode, and the KV rays are emitted to realize an independent cone beam, fan beam or spiral CT scanning; and/or before and/or after therapy, the first PET detector 31 and/or the second PET detector 32, the KV ray source 20 are set to the counting mode, the KV rays are emitted, and the KV ray photons and the gamma ray generated by the positron annihilation are distinguished by the energy threshold of the light counting detector to perform the PET scanning and the CT scanning simultaneously.

When the CT scanning is performed, the KV ray source 20 and the first PET detector 31 and the second PET detector 32 are rotated relative to the object around the object to obtain the CT data at different rotation angles.

The tomographic imaging and image-guided radiation therapy apparatus according to the present disclosure may have the following two modes in therapy:

the KV ray source emits beams in a pulsed manner through the pulse interval of a pulsed therapy, to perform the CT imaging and the therapy simultaneously; and/or the first PET detector 31 and/or the second PET detector 32, the KV ray source 20 are set to the counting mode, the KV ray source emits beams in the pulsed manner through the pulse interval of the pulsed therapy, and the KV ray photons and the gamma ray generated by the positron annihilation are distinguished by the energy threshold of the light counting detector to perform the CT imaging, the PET imaging, and the therapy synchronously.

It should be noted that the three modes before and/or after therapy, and the two modes in therapy may be optionally combined.

The imaging mode in therapy may be combined with any one of the imaging modes before and after therapy to realize various imaging functions of the tomographic imaging and image-guided radiation therapy apparatus.

With CT data acquired by scanning, a CT image is obtained through an analytical image reconstruction algorithm or iterative image reconstruction algorithm by computer calculation. The obtained CT data or CT images can be used to assist the PET imaging and/or the PET-guided radiation therapy, correct an attenuation in reconstructing the PET image, motion artifact, and the like, and can also be used directly to guide the radiation therapy.

In some other embodiments, the KV ray source 20 of the tomographic imaging and image-guided radiation therapy apparatus may be a plurality of ray sources. The KV ray source 20 may also be placed on the first PET detector 31 or at the inner side of the first PET detector 31 (the side facing the object). In the two cases, it is not necessary to provide an opening in the first PET detector.

Figure 5:
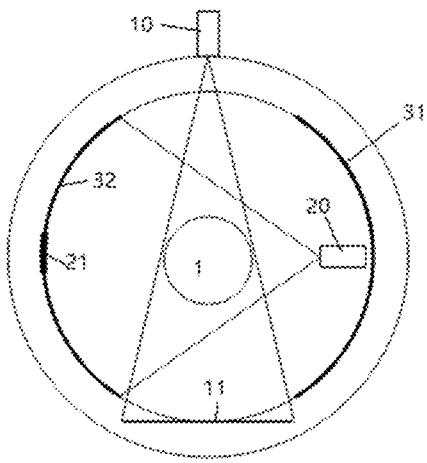
FIG. 5 is a schematic view showing a structure of a second implementation of FIG. 1.
Figure 6:
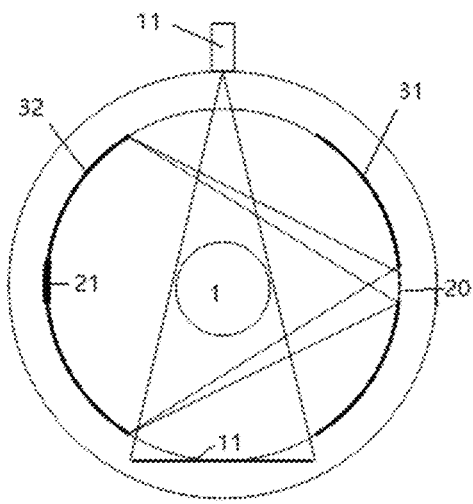
FIG. 6 is a schematic view showing a structure of a third implementation of FIG. 1.
Figure 7:
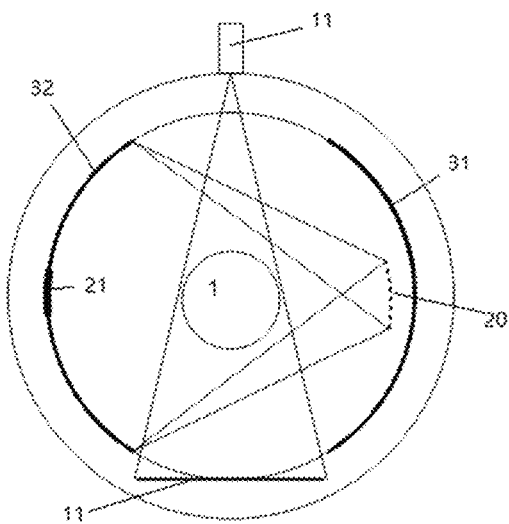
FIG. 7 is a schematic view showing a structure of a fourth implementation of FIG. 1.

As shown in FIGS. 5 to 7, sequentially shown are a single KV ray source 20 placed on the inner side of the first PET detector 31 in the second embodiment, a plurality of KV ray sources 20 placed on the first PET detector 31 in the third embodiment, and a plurality of KV ray sources 20 placed at the inner side of the first PET detector 31 in the fourth embodiment. These embodiments are similar to the first embodiment and are no longer described herein for the sake of brevity.

Figure 8:
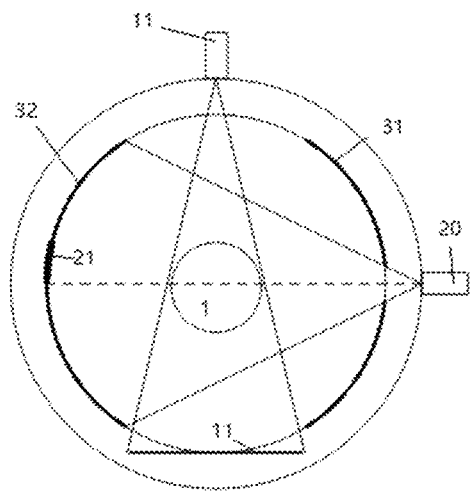
FIG. 8 is a schematic view showing a structure of a fifth implementation of FIG. 1.
Figure 9:
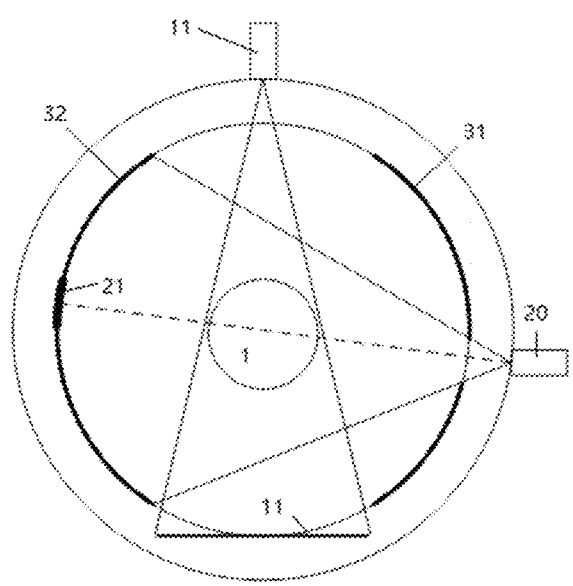
FIG. 9 is a schematic view showing a structure of a sixth implementation of FIG. 1.

FIG. 8 is a schematic view showing a structure of a fifth implementation of FIG. 1, and FIG. 9 is a schematic view showing a structure of a sixth implementation of FIG. 1. Referring to FIGS. 2, 8, and 9 again, The second PET detector 32 and the CT detector 21 in FIG. 2 as a whole are symmetrical about the KV central ray beam, and the second PET detector 32 and the CT detector 21 in FIGS. 8 and 9 as a whole are asymmetric about the KV central ray beam. In the example shown in FIG. 9, the first PET detectors 31 on a side of the KV ray source 20 are also asymmetric about the KV ray source 20. In general, the first implementation in FIG. 2 is preferred, that is, the second PET detector 32 and the CT detector as a whole are symmetrical about the KV central ray beam, which can make the ray beam received by the whole detector more uniform.

In summary, in the tomographic imaging and image-guided radiation therapy apparatus according to the present disclosure, the CT detector 21 is disposed between the second PET detectors 32, which helps to improve the detection sensitivity of the tomographic imaging and image-guided radiation therapy apparatus, and at the same time helps to improve the spatial resolution of the CT imaging and reduce scattering artifacts, without significantly reducing the performance of the PET imaging of the system.

Unless well-known as contrary, the numerical parameters in the present specification and the appended claims are approximate values and can be changed according to the desired characteristics obtained by the contents of the present disclosure. Specifically, all numbers used in the specification and claims to indicate the content of the composition, reaction conditions, etc., should be understood as modified by the word "about" in all cases. In general, the meaning of the expression refers to including a specific amount with ±10% change in some embodiments, ±5% change in some embodiments, ±1% change in some embodiments, ±0.5% change in some embodiments.

Furthermore, "comprising" does not exclude the presence of elements or steps not listed in a claim. The presence of "a" or "an" before an element does not exclude the presence of a plurality of such elements.

The ordinal numbers used in the specification and claims, such as "first", "second", "third", etc., are used to modify respective elements, which itself neither means that the elements have any ordinal numbers, nor represents the order of an element and another element, or the order of a manufacturing method. These ordinal numbers are used only to distinguish an element with a name from another element with the same name clearly.

The object, technical solutions, and advantageous effect of the present disclosure are further described in detailed in the above specific embodiments. It should be appreciated that the above description is only specific embodiments of the present disclosure and the embodiment is not used to limit the present disclosure. It will be understood by those skilled in the art that various modifications, equivalent substitutions and improvements may be made therein without departing from the principles and spirit of the present disclosure and fall within the scope of the present disclosure.

What is claimed is:

1. A tomographic imaging and image-guided radiation therapy apparatus comprising:
   at least one high-energy ray source;
   at least one KV ray source for providing KV ray for medical diagnosis;
   a first PET detector located on a side close to the at least one KV ray source,
   a second PET detector located on a side away from the at least one KV ray source and at the side opposite to the KV ray source: and
   a CT detector located at the side opposite to the KV ray source and configured to receive the KV ray for CT imaging;
   wherein the at least one KV ray source is placed on or at an inner side of or at outer side of the first PET detector;
   the second PET detector and the CT detector are configured to receive the KV ray to perform KV CT imaging;
   the first PET detector and the second PET detector are further configured to receive a gamma ray emitted by an object to perform a PET imaging;
   the high-energy ray source is configured to generate a high-energy ray for radiation therapy of the object;
   the KV CT imaging of the CT detector and the second PET detector and/or the PET imaging of the first PET detector and the second PET detector are configured to assist and/or guide the radiation therapy of the object.

2. The tomographic imaging and image-guided radiation therapy apparatus of claim 1, wherein there is an intersection point between the CT detector and a straight line where a focal point of the KV ray source and a center of the object are located, and a distance between the intersection point and a center of the CT detector is not greater than a half of a length of the CT detector.

3. The tomographic imaging and image-guided radiation therapy apparatus of claim 2, wherein the focal point of the KV ray source, the center of the object, and a position offset from the center of the CT detector by (n+1/4)–a lie on a same straight line, where a is a detector pixel of the CT detector, n is an integer, and 0≤n≤8.

4. The tomographic imaging and image-guided radiation therapy apparatus of claim 1, wherein the CT detector is an energy integrating detector or a photon counting detector; and/or
the KV ray source comprises one of an X-ray tube, a carbon nanotube, or an isotope source; the KV ray is an X-ray or a gamma ray; and/or
the high-energy ray source comprises an accelerator or an isotope source for radiation therapy, the high-energy ray comprises one of a MV photon ray or a MV particle ray, and the MV photon ray comprises one of a MV order X-ray or a gamma ray; and the MV particle ray comprises one of a proton, a neutron or a carbon ion.

5. The tomographic imaging and image-guided radiation therapy apparatus of claim 1, wherein the first PET detector and the second PET detector are composed of a plurality of PET detection modules and/or a plurality of detection units, there is gap between adjacent ones of the PET detection modules and/or the detection units, and the first PET detector and the second PET detector have an arc shape, a straight line shape, or a polygonal shape.

6. The tomographic imaging and image-guided radiation therapy apparatus of claim 1, wherein the CT detector is equipped with at least one de-scattering processing unit with a function of removing scattered photons, a spatial structure of the de-scattering processing unit is a one-dimensional fence or a two-dimensional grid, and a material of which the fence and/or the grid is made is a metal with a high atomic number.

7. The tomographic imaging and image-guided radiation therapy apparatus of claim 1, wherein the CT detector has the same detector pixel and scintillator thickness and is of the same type as the PET detector.

8. The tomographic imaging and image-guided radiation therapy apparatus of claim 1, wherein the CT detector is a flat detector with a high spatial resolution, the high spatial resolution means that a detector pixel of the flat detector is not greater than 1 mm, and the CT detector is further configured to receive the KV ray to perform a single-frame or multi-frame transmissive imaging.

9. The tomographic imaging and image-guided radiation therapy apparatus of claim 1, wherein the second PET detector and the CT detector are configured to receive the KV ray to perform the KV CT imaging in such a way that:
the CT detector receives the KV ray, a scattering correction is performed on the KV ray received by the second PET detector, and data and/or image are combined and processed to determine a KV CT image of a full field of view; or
the second PET detector receives the KV ray, a data truncation correction and a scattering correction optimization is performed on the KV ray received by the CT detector to determine a KV CT image of a partial field of view.

10. The tomographic imaging and image-guided radiation therapy apparatus of claim 1, further comprising: at least one high-energy detector placed opposite to the high-energy ray source and configured to receive a high-energy ray;
the high-energy detector, the high-energy ray source, the first PET detector, the second PET detector and the CT detector, and the KV ray source are located in a same plane; and
the first PET detector and the second PET detector are located on two sides of the high-energy ray source and the high-energy detector, respectively.

11. The tomographic imaging and image-guided radiation therapy apparatus of claim 1, further comprising:
a rotating gantry configured to carry the first PET detector, the second PET detector, the CT detector, the high-energy ray source and the KV ray source, and rotate the first PET detector, the second PET detector, the CT detector, the high-energy ray source and the KV ray source around the object; and
a mechanical/electrical control and data transmission/processing unit configured to control the rotating gantry, the first PET detector, the second PET detector, the CT detector, the high energy ray source and the KV ray source, and transmit and process data detected by the first PET detector and the second PET detector, the CT detector.

12. The tomographic imaging and image-guided radiation therapy apparatus of claim 1, wherein the first PET detector and the second PET detector are centrally symmetric about the object.

* * * * *